US009662021B2

(12) United States Patent
Chow et al.

(10) Patent No.: US 9,662,021 B2
(45) Date of Patent: May 30, 2017

(54) MINIATURE STENT-BASED IMPLANTABLE WIRELESS MONITORING DEVICES

(75) Inventors: Eric Y. Chow, Colorado Springs, CO (US); Brooke Beier, East China, MI (US); William J. Chappell, West Lafayette, IN (US); Pedro P. Irazoqui, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 86 days.

(21) Appl. No.: 12/685,917

(22) Filed: Jan. 12, 2010

(65) Prior Publication Data
US 2010/0179449 A1    Jul. 15, 2010

Related U.S. Application Data

(60) Provisional application No. 61/143,965, filed on Jan. 12, 2009.

(51) Int. Cl.
| | | |
|---|---|---|
| *A61B 5/0215* | (2006.01) | |
| *A61B 5/07* | (2006.01) | |
| *A61B 5/00* | (2006.01) | |
| *A61F 2/82* | (2013.01) | |

(52) U.S. Cl.
CPC ............ *A61B 5/0215* (2013.01); *A61B 5/076* (2013.01); *A61B 5/6862* (2013.01); *A61B 5/6876* (2013.01); *A61B 5/6882* (2013.01); *A61F 2/82* (2013.01); *A61B 2562/028* (2013.01); *A61F 2250/0002* (2013.01)

(58) Field of Classification Search
CPC ... A61B 5/0031; A61B 5/6862; A61B 5/6876; A61B 5/026; A61B 5/0215; A61B 5/02152; A61B 5/02154; A61B 5/02156; A61B 5/02158; A61B 2560/0214; A61B 2560/0219
USPC ........ 600/485, 486, 488, 500, 504, 505, 561
See application file for complete search history.

(56) References Cited

U.S. PATENT DOCUMENTS

| | | | |
|---|---|---|---|
| 5,147,392 A | | 9/1992 | Inagaki et al. |
| 5,967,986 A | * | 10/1999 | Cimochowski et al. ..... 600/454 |
| 6,053,873 A | * | 4/2000 | Govari et al. ................ 600/505 |
| 6,277,078 B1 | * | 8/2001 | Porat et al. ................... 600/486 |
| 6,708,065 B2 | * | 3/2004 | Von Arx et al. ................ 607/60 |
| 6,840,956 B1 | * | 1/2005 | Wolinsky et al. ............ 623/1.13 |
| 2005/0060011 A1 | * | 3/2005 | Denker et al. .................. 607/60 |
| 2005/0065592 A1 | | 3/2005 | Holzer |
| 2005/0080346 A1 | * | 4/2005 | Gianchandani et al. ..... 600/486 |
| 2006/0129050 A1 | * | 6/2006 | Martinson et al. ........... 600/505 |
| 2009/0062900 A1 | * | 3/2009 | Lal et al. ..................... 623/1.15 |
| 2011/0036173 A1 | * | 2/2011 | Chommeloux et al. ........ 73/702 |

OTHER PUBLICATIONS

PCT Search Report dated Mar. 18, 2010 of Patent Application No. PCT/US2010/020737 filed Jan. 12, 2010.

* cited by examiner

*Primary Examiner* — Adam J Eiseman
(74) *Attorney, Agent, or Firm* — Maginot, Moore & Beck LLP

(57) ABSTRACT

A system is provided for the transmission of in vivo arterial pressure, the system comprising: an a pressure sensor whereby in vivo arterial pressure data is collected; a wireless transmitter, whereby the in vivo arterial pressure data is transmitted to be received disposed externally to a patient in which the system is disposed; a stent body, the stent body having an integral antenna, and a power source, whereby power is supplied to the system.

19 Claims, 5 Drawing Sheets

MINIATURE STENT-BASED IMPLANTABLE WIRELESS MONITORING DEVICES

RELATED APPLICATIONS

This application claims the benefit of U.S. Provisional Application No. 61/143,965, filed Jan. 12, 2009. This application is herein incorporated by reference in its entirety for all purposes.

FIELD OF THE INVENTION

The invention relates to medical devices, and more particularly, to a medical device having an implantable stent with a wireless monitoring device.

BACKGROUND OF THE INVENTION

Heart failure is a disabling and often deadly condition affecting approximately 2% of the adult population in developed countries and 6-10% of people over the age of 65. For a middle-aged person living in Europe or North America, there is a one in five chance of him or her developing heart failure. After a patient has been diagnosed with heart failure, there is a 30-40% chance of death within the first year, and after 5 years, this percentage increases to 60-70%.

It is possible to detect heart failure through monitoring of the pressures within the heart. The heart can be broken down into two sides: left and right. Each side has a "feeding" chamber called the atrium, and a "working" chamber called the ventricle. The main purpose of the atria is to maintain and regulate the filling of the ventricles. The filling pressure of a ventricle is the most important hemodynamic parameter reflecting its state and mechanical output. The so called 'Starling Law' of the heart describes the property that inside a certain range, the mechanical output of the heart, whether in terms of volume pumped or work produced, depends on the filling pressure. An extension of this property is that when heart failure occurs, the whole of the cardiovascular system, including arteries, veins, kidneys, and a whole range of complex hormonal mechanisms, will attempt to compensate to increase the filling pressures of both ventricles. This is accomplished through various mechanisms including retention of water and salt, centralization of intravascular volume, and venoconstriction. As a result, more blood comes to fill the atria which increase the filling pressures of both ventricles. This initially solves the problem of decreased cardiac output, but eventually it turns into a vicious circle, where insufficient heart power and work is detected by the system and the filling pressures of the heart are further increased. Soon these increases in filling pressures become intolerable and problems including breathlessness and pulmonary congestion ensue. As a result, the most reliable and constant parameter that reflects the situation of heart failure is the increase of the filling pressures, namely, the mean pressures of both atria. These pressures are more constant and reliable than a measure of decrease in pumped volume.

The most useful parameter for diagnosing heart failure is the filling pressure of the left ventricle. The work done by left ventricle is about 3-5 times the work done by the right, producing high pressures around 100 to 150 mmHg, while the right ventricle works at a range of 15 to 30 mmHg. Most diseases attack first, and sometimes exclusively, the left ventricle and if a disease affects both ventricles, the first to suffer is the left one. The filling pressure of the left ventricle is exactly the mean pressure of the left atrium. It is possible to derive the filling pressure of the left ventricle from its pressure curve, but the curve must be very detailed and you must look at the instantaneous pressure at the end of diastole, which is a certain point in the curve that visually is sometimes difficult to determine. The easiest measure of left ventricular filling pressure and heart performance is the mean pressure of the left atrium.

The mean left atrial pressure is exactly equal to the pressure in a distal pulmonary artery after occluding it, measuring distally to the occlusion, which is called pulmonary capillary wedge pressure (PCWP). Obtaining PCWP in a long term monitoring system may not be feasible since occlusion would likely cause the vessel to become thrombosed and possibly resulting in a loss or change of pressure. A free-floating pressure in the pulmonary artery is called the pulmonary artery diastolic pressure (PADP), which is also a good index of left ventricular filling and the difference between PADP and PCWP is small and generally fixed for each patient. These pressures are extremely useful and allow for the diagnosis of heart failure, estimations of severity and can be used to monitor response to treatment, evolution and prognosis.

Stents have a variety of applications and are most widely used in treating obstruction of blood flow in the cardiovascular system. A common problem with stents is reocclusion, although current technologies employed to alleviate this problem include the incorporation of drug-eluting coatings as well as using careful consideration when choosing base materials. Even with these preventative measures, re-occlusion can still occur without warning since little is known about the performance of stents after initial placement.

A device that monitors pressure in the surrounding area, as well as blood flow and temperature, would provide clinicians with a method for monitoring PADP, and therefore PCWP, and would provide information regarding how well the stent is faring in the implanted environment. Fully wireless operation as well as integration with the stent is crucial for such a device monitoring device. Current wireless cardiac pressure sensor devices require either a clinical visit or manual interrogation of the device using an external transmitter and receiver. This limits the overall effectiveness of the system by relying on the patient or a clinician to initiate collection of diagnostic data.

What is needed therefore is a completely wireless implantable system implanted in the pulmonary artery and having fully wireless capability, in terms of both telemetry and powering, through the chest wall to record cardiac diagnostics at fixed intervals without manual intervention.

SUMMARY OF THE INVENTION

One embodiment of the present invention provides a system for the transmission of in vivo arterial pressure, the system comprising: a pressure sensor whereby in vivo arterial pressure data is collected; a wireless transmitter, whereby the in vivo arterial pressure data is transmitted to be received disposed externally to a patient in which the system is disposed; on-board memory for storage of sensor data, to be transmitted to an external receiver at regular intervals; a stent body, the stent body having an integral antenna, and a power source, whereby power is supplied to the system.

Another embodiment of the present invention provides such a system wherein the power source is a Radio Frequency power reception and storage system.

A further embodiment of the present invention provides such a system wherein the pressure sensor, the transmitter, and the power source are disposed on an outboard side of the stent, and proximal to an arterial wall such that blood flow through the stent is substantially unobstructed by the system when installed.

A yet still further embodiment of the present invention provides such a system wherein the antenna is a dipole or monopole.

A yet further embodiment of the present invention provides such a system wherein the antenna further comprises a balun.

Still another embodiment of the present invention provides such a system further comprising a second stent body.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

Figure 1:
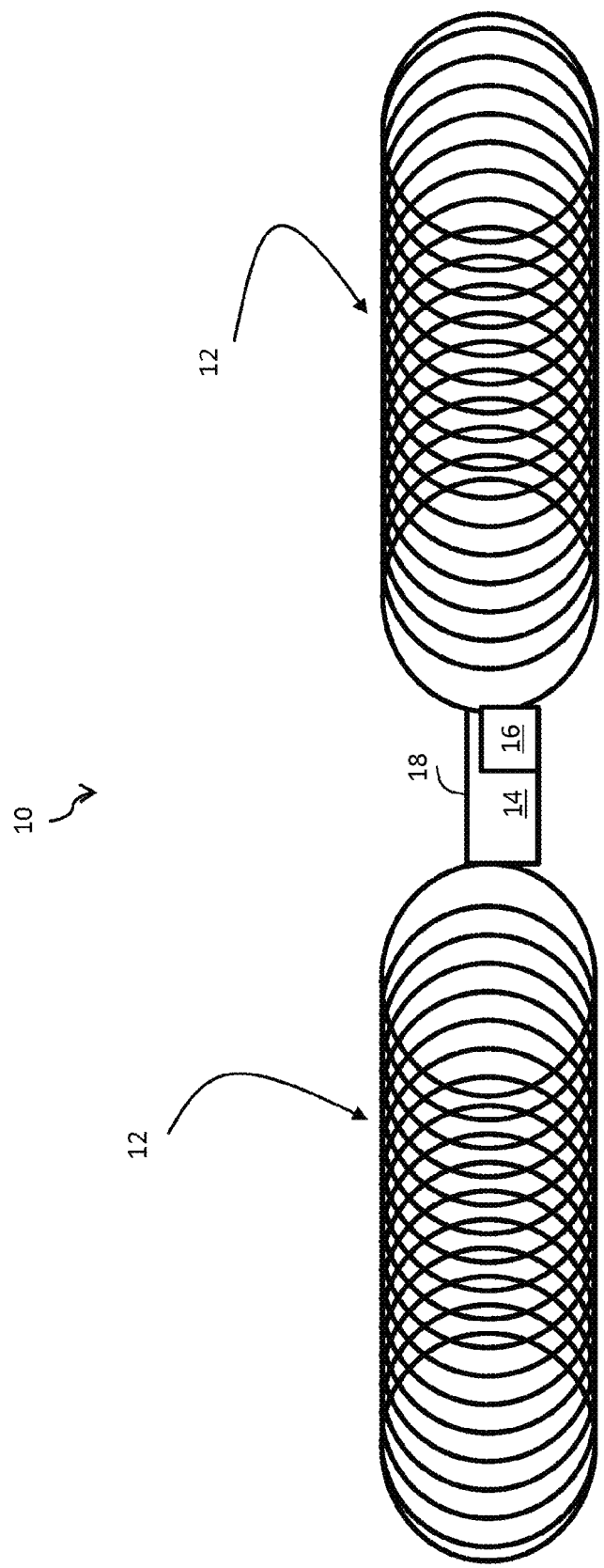
FIG. 1 is a block diagram illustrating a implantable sensor platform with integrated double stent and configured in accordance with one embodiment of the present invention.
Figure 2:
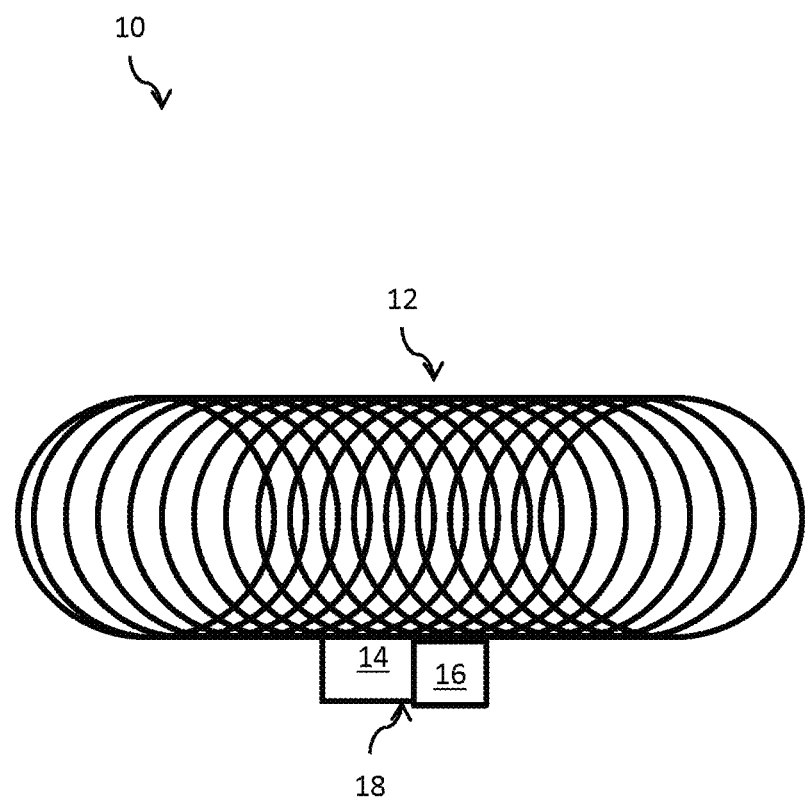
FIG. 2 is a block diagram illustrating a implantable sensor platform with integrated stent and configured in accordance with one embodiment of the present invention.

One embodiment of the present invention provides an implantable internal cardiac pressure monitor as illustrated in FIGS. 1 and 2. Such a device incorporates stents 12 into the overall structure, which acts as structural support, anchor, and antenna for the implant. Cardiac stents are widely used to treat ischemic disease, and their safety, sustainability, and delivery methods are well established.

All biomedical implants face stringent requirements on their size and shape. A stent-based cardiac monitoring implant, configured according to one embodiment of the present invention, would face the restrictions imposed by the vessel walls. In such an embodiment, a dipole topology allows efficient use of available area and provides a simple structure that can be implemented using stents. To facilitate meeting this size limitation is the inclusion of a micro-sized pressure sensor and electronics.

In one embodiment of the stent-based transmitter illustrated in FIG. 1, two stents 12 were integrated with a voltage controlled oscillator (VCO). The VCO chip 14 was soldered onto a standard SOIC8-to-DIP adapter PCB 18 along with the stents 12 and power source 16.

In one embodiment of the system illustrated in FIG. 2, a miniaturized system 14 is attached to the outer surface of a regular balloon expandable, self-expandable, or drug-eluting FDA approved stent 12. When expanded, the stent 12 maintains un-constricted flow while allowing contact between the electronic sensors and the blood supply. The stent 12 doubles as an antenna for wireless telemetry of data from within the blood vessel, and wireless power supply to the implanted electronics. Additionally, this stent 12 provides structural support and tissue anchoring to the device. Using the stent platform as both a radiating antenna and structural support allows us to take advantage of an FDA approved device whose safety has been verified and whose surgical procedure is well established.

The electronics package 14 is reduced to a size of less than 1 mm2, with a thickness of under 300 µm. A minimally-invasive implantation procedure allows the delivery of the stent-based implant 10 in nearly any major vessel of the body. The particular embodiment of FIG. 1 describes an initial prototype with two stents 12, a 2.4 GHz transmitter microchip 14, and a battery 16. The transcutaneous transmission has been validated through ex vivo and in vivo pig studies, demonstrating the feasibility of a stent-based wireless platform for continuous monitoring of blood pressure, blood flowrate, and chemical composition of the blood.

Figure 3:
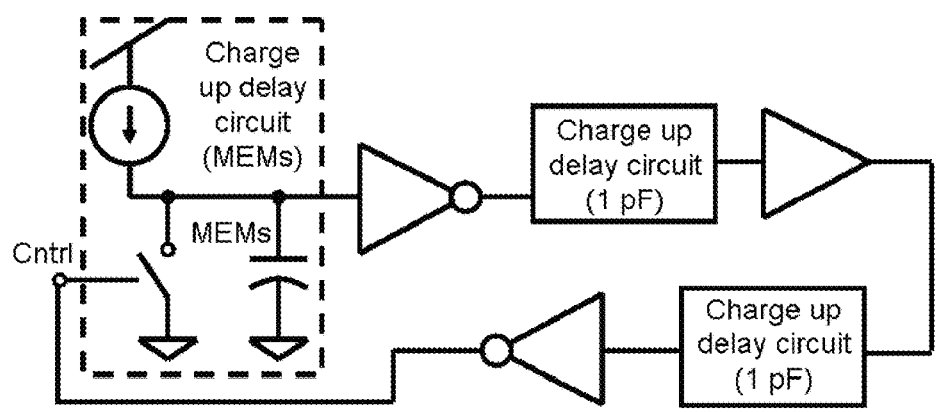
FIG. 3 is a block diagram illustrating a sensor interface configured in accordance with one embodiment of the present invention.

The various embodiments of the present invention provide integration of a micro-sized capacitive-pressure sensor 14. An interface for the pressure sensor and a wireless transmitter was designed on the Texas Instruments 130 nm CMOS process. A micro-electro-mechanical systems (MEMS) capacitive sensor is used for converting pressure variations to capacitance changes. The sensor produces 3.3 fF changes for 0.5 mmHg changes. The sensor interface, shown in FIG. 3, converts the capacitance change to time variations. The fundamental block of the circuit consists of a current source which feeds charge into the top plate of the capacitive sensor. The capacitor is attached to a Schmitt trigger so once the top plate is charged to above the threshold of the trigger, the pulse stops. The pulse starts when the current source begins feeding the capacitor and stops once the capacitor is charged to the trigger threshold. The width of this pulse is directly proportional to the capacitance of the sensor and varies by 1 µs as for every 2 fF change in capacitance. Two additional delay blocks are added in series to form a closed loop with the fundamental block to produce an oscillator structure which repeats every millisecond. Thus, a new pulse is produced every millisecond resulting in a 1 kHz sampling frequency.

Figure 4A:
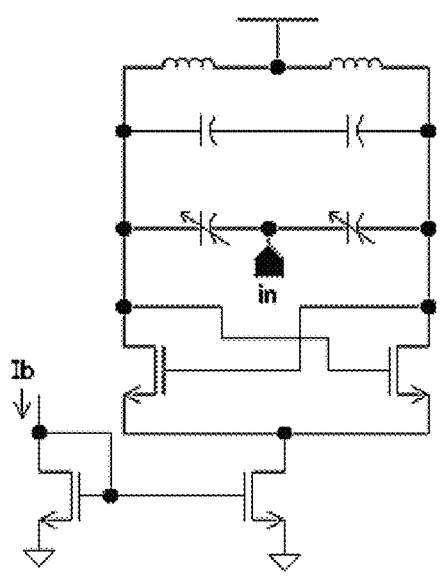
FIG. 4A is a block diagram illustrating a NMOS cross-coupled pair VCO configured in accordance with one embodiment of the present invention.
Figure 4B:
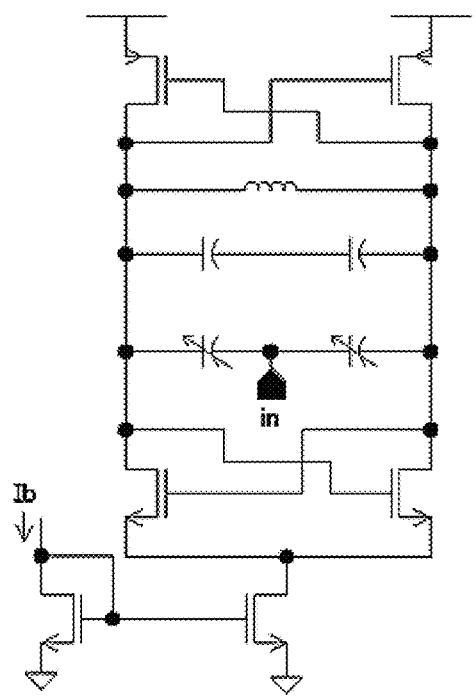
FIG. 4B is a block diagram illustrating a complementary cross-coupled pair VCO configured in accordance with one embodiment of the present invention.

This pulse width modulated signal is then fed into a voltage controlled oscillator (VCO). For frequency modulation a direct input-voltage to frequency conversion is done using a voltage-controlled oscillator (VCO). A popular VCO topology is the NMOS cross-coupled pair shown in FIG. 4(a). However, there are several benefits to using the complementary structure shown in FIG. 4(b). One advantage is that for a given current, the complementary structure has twice the output voltage amplitude, which leads to better phase noise. Furthermore, a complementary architecture has a more symmetric output waveform and thus further reduces the amount of phase noise. One disadvantage is that the complementary topology has a lower tuning range for a given transconductance. For our VCO design, a complementary cross-coupled pair topology due to its lower power consumption for comparable performance.

The final topology works as an inductor-capacitor (LC) tank circuit whose frequency of oscillation is determined by $$f = \frac{1}{2\pi\sqrt{Lc(V_{in})}}$$

In (1), C(Vin) is the parallel combination of a tank capacitor and the varactor capacitances as a function of Vin. This variation of capacitance with input-voltage produces the range of frequency variation. The tank capacitor is used to tune the oscillation frequency to the desired operating-frequency. The tank inductor, L, is placed between the two VCO branches to ensure that both ends are biased at the same DC voltage to maintain a symmetric output. The inductor is a direct path between branches at DC but presents a high impedance to high-frequency voltage-signals thus producing a high-Q oscillator when placed in parallel with the tank capacitance.

The powering components of the ASIC consist of a voltage regulator, bandgap voltage references, and a radio frequency (RF) powering unit. The RF powering circuit uses a high frequency rectifier topology consisting of an 8 stage array of RF capacitors and Schottky diodes. The rectifier converts a GHz wave into a DC supply for the rest of the ASIC.

Figure 5:
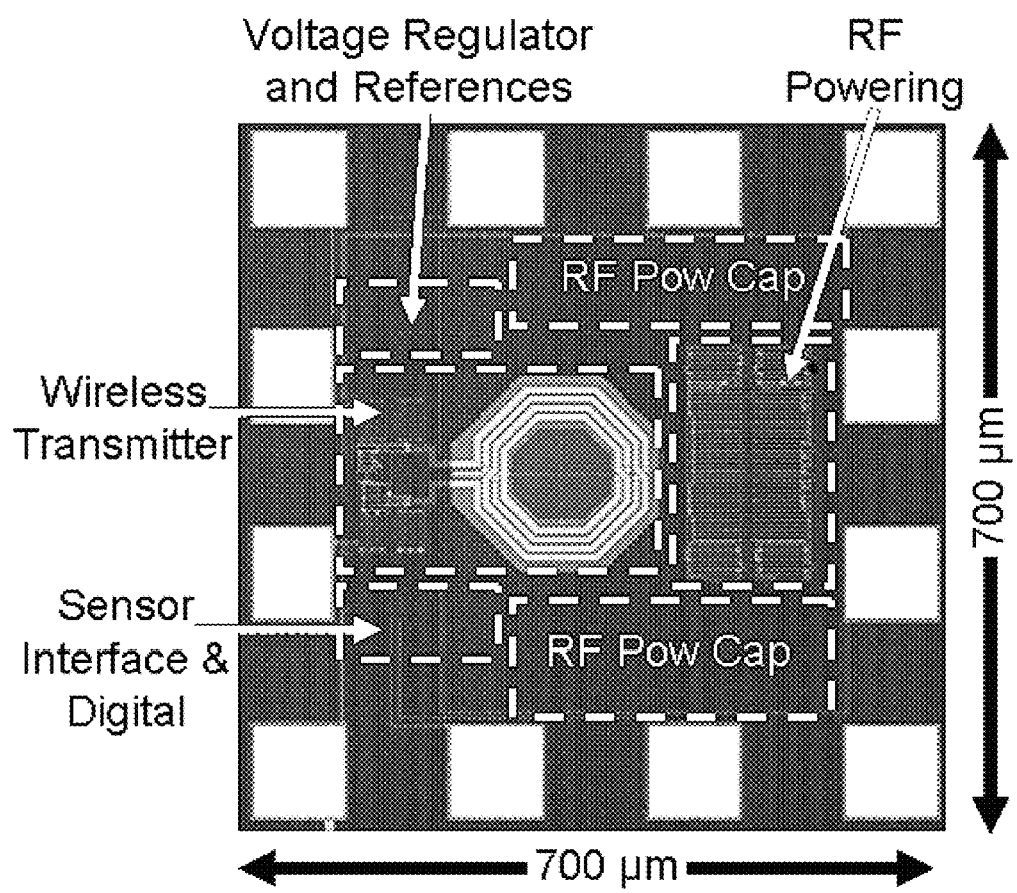
FIG. 5 is a photograph illustrating an ASIC configured to be integrated with an implantable sensor platform with integrated stent and configured in accordance with one embodiment of the present invention.

The full layout of the design, shown in FIG. 5, is composed of the sensor interface, wireless transmitter, voltage regulator and references, RF powering block, and testing pads.

In another embodiment of the device, the implanted sensor and external device will allow for continuous, remote monitoring of cardiac metrics, such as mean left atrium pressure, systole and diastole pressure, blood flowrate, and chemical composition of the blood. Through an external receiver and transmitter, the device can store enough power and data to operate continuously, uploading data at 24-hour intervals to be securely transmitted to a central data repository. This system enables a clinician to remotely monitor a patient's symptoms, minimizing clinical visits and improving the quality of care.

Internal monitoring of the cardiovascular system would be useful for clinicians to diagnose and treat conditions including cardiac disease and heart failure. To maximize versatility, the monitoring implant should be miniature and completely wireless, while not relying on patient or clinical intervention to record pressure, flow, or chemistry data remotely. One embodiment of the present invention provides a platform based on the use of medical stents as both radiating antennas and structural support. The use of stents allows us to take advantage of an FDA approved device whose safety has been verified and whose surgical procedure is well established. This low-invasive percutaneous implantation procedure allows the delivery of a miniature stent-based implant in nearly any vessel of the body. One embodiment was developed integrating two stents, a 2.4 GHz transmitter integrated circuit, and a battery and quantified transcutaneous transmission through ex vivo and in vivo studies.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A system for the transmission of in vivo arterial pressure, the system comprising:
    a pressure sensor configured to collect in vivo pulmonary arterial pressure data continuously at a predetermined frequency;
    a radio transmitter configured to transmit said in vivo pulmonary arterial pressure data to be received externally of a patient in which said system is disposed;
    a stent coil body proximate to said pressure sensor and configured to tissue anchor said system, said stent coil body forming an antenna;
    a radio power source configured to receive and store power via radio waves transmitted to said antenna; and
    a remote monitor of in vivo arterial pressure external to the patient configured to communicate with said radio transmitter,
    wherein said radio transmitter and said antenna cooperate to generate transmissions to said remote monitor.

2. The system according to claim 1 wherein said pressure sensor, said transmitter, and said radio power source are disposed on an outboard side of said stent coil body, and proximal to an arterial wall such that blood flow through said stent coil body is substantially unobstructed by said system when installed.

3. The system according to claim 1 further comprising a data storage device configured to store said data until transmission to said remote monitor.

4. The system according to claim 1 wherein said antenna is a dipole.

5. The system according to claim 4 wherein said antenna further comprises a balun.

6. The system according to claim 1 wherein said antenna is a monopole.

7. The system according to claim 4 wherein said antenna further comprises a balun.

8. The system according to claim 1 further comprising a second stent coil body.

9. The system according to claim 1 further comprising a flowrate sensor.

10. The system according to claim 1 further comprising a system for detecting systole and diastole pressure.

11. The system according to claim 1 further comprising a blood chemistry sensor.

12. An apparatus for monitoring in vivo circulatory data of a subject, said apparatus comprising:
    a stent coil body forming an antenna configured to be disposed in a pulmonary vessel, and said stent coil body configured to tissue anchor said apparatus to said pulmonary vessel;
    a sensor package coupled to said stent coil body so as not to obstruct said pulmonary vessel;
    a transmitter, coupled to said antenna, configured to transmit data from the said sensor package on a continuous basis to receivers external to said subject using radio transmissions; and
    a radio power charging and storage system disposed within said apparatus configured to receive, store and supply power to said sensor package, said antenna, and said transmitter.

13. The apparatus according to claim 12 wherein said sensor package comprises a flowrate sensor.

14. The apparatus according to claim 12 wherein said sensor package comprises a pressure sensor.

15. The apparatus according to claim 12 wherein said sensor package senses blood chemistry.

16. The apparatus according to claim 12 wherein said sensor package comprises a system for detecting systole and diastole pressure.

17. The apparatus according to claim 12 wherein said sensor package, said transmitter, and said power source are disposed on an outboard side of said stent coil body, and proximal to a wall of said pulmonary artery such that blood flow through said stent coil body is substantially unobstructed by said system when installed.

18. The apparatus according to claim 12 wherein said antenna further comprises a balun.

19. The system of claim 1 wherein said radio transmitter is a transceiver configured to receive data from an external transmitter.

* * * * *